United States Patent
Miyamoto

(10) Patent No.: US 11,419,567 B2
(45) Date of Patent: Aug. 23, 2022

(54) RADIOGRAPHIC SYSTEM AND RADIOGRAPHIC METHOD FOR OBTAINING A LONG-SIZE IMAGE AND CORRECTING A DEFECTIVE REGION IN THE LONG-SIZE IMAGE

(71) Applicant: CANON KABUSHIKI KAISHA, Tokyo (JP)

(72) Inventor: Hideaki Miyamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 117 days.

(21) Appl. No.: 16/844,687

(22) Filed: Apr. 9, 2020

(65) Prior Publication Data
US 2020/0229784 A1 Jul. 23, 2020

Related U.S. Application Data

(63) Continuation of application No. 15/006,619, filed on Jan. 26, 2016, now Pat. No. 10,695,024.

(30) Foreign Application Priority Data

Jan. 30, 2015 (JP) ................................. 2015-017890

(51) Int. Cl.
*A61B 6/00* (2006.01)
*H04N 5/32* (2006.01)
*G06T 5/50* (2006.01)
*H04N 5/341* (2011.01)
*H04N 5/217* (2011.01)
(Continued)

(52) U.S. Cl.
CPC .............. *A61B 6/5241* (2013.01); *A61B 6/42* (2013.01); *A61B 6/4208* (2013.01); *A61B 6/4266* (2013.01); *A61B 6/52* (2013.01); *A61B 6/5235* (2013.01); *A61B 6/5252* (2013.01); *A61B 6/5258* (2013.01); *A61B 6/582* (2013.01); *A61B 6/586* (2013.01); *G06T 5/005* (2013.01); *G06T 5/009* (2013.01); *G06T 5/50* (2013.01); *H04N 5/2176* (2013.01); *H04N 5/23238* (2013.01); *H04N 5/32* (2013.01); *H04N 5/3415* (2013.01); *H04N 5/367* (2013.01); *G06T 2207/10116* (2013.01)

(58) Field of Classification Search
CPC ....... A61B 6/42; A61B 6/4208; A61B 6/4266; A61B 6/52; A61B 6/5205; A61B 6/5211; A61B 6/5235; A61B 6/5241; A61B 6/5258
USPC .............. 378/62, 98.12, 145, 189, 196, 197; 250/370.09
See application file for complete search history.

(56) References Cited

U.S. PATENT DOCUMENTS 6,273,606 B1 * 8/2001 Dewaele .............. A61B 6/5241
378/174
6,463,121 B1 * 10/2002 Milnes .................. A61B 6/469
378/62

(Continued)

*Primary Examiner* — Allen C. Ho
(74) *Attorney, Agent, or Firm* — Canon U.S.A., Inc. IP Division

(57) ABSTRACT

The radiographic system including a plurality of radiation detection apparatuses, which detect radial rays, a combining processor which generates a long-size image by combining a plurality of radiation images obtained from the radiation detection apparatuses, and an image correction unit, which corrects a defective region in which the plurality of radiation detection apparatuses overlap with each other in the long-size image.

20 Claims, 9 Drawing Sheets

(51) Int. Cl.
*H04N 5/367* (2011.01)
*G06T 5/00* (2006.01)
*H04N 5/232* (2006.01)

(56) References Cited

U.S. PATENT DOCUMENTS

| | | | | |
|---|---|---|---|---|
| 6,895,106 B2* | 5/2005 | Wang | ............... | A61B 6/5241 |
| | | | | 382/132 |
| 7,522,701 B2* | 4/2009 | Jensen | ............... | A61B 6/481 |
| | | | | 378/162 |
| 7,742,570 B2* | 6/2010 | Yamaguchi | ......... | A61B 6/5241 |
| | | | | 378/98.12 |
| 7,978,816 B2* | 7/2011 | Matsuura | ............ | A61B 6/5241 |
| | | | | 378/62 |
| 8,344,327 B2* | 1/2013 | Yamaguchi | ......... | A61B 6/5241 |
| | | | | 250/363.07 |
| 8,360,639 B2* | 1/2013 | Kato | ............... | A61B 6/4441 |
| | | | | 378/197 |
| 8,586,934 B2* | 11/2013 | Nakatsugawa | ...... | G01T 1/2985 |
| | | | | 250/363.02 |
| 8,748,834 B2* | 6/2014 | Enomoto | ........... | H04N 5/3415 |
| | | | | 250/370.08 |
| 8,767,913 B2* | 7/2014 | Okuno | ............... | G01N 23/04 |
| | | | | 378/62 |
| 8,792,616 B2* | 7/2014 | Tanaka | .............. | A61B 6/527 |
| | | | | 378/95 |
| 8,899,832 B2* | 12/2014 | Fabrizio | ............. | A61B 6/08 |
| | | | | 378/196 |
| 9,016,940 B2* | 4/2015 | Fabrizio | ............. | A61B 6/4405 |
| | | | | 378/177 |
| 9,078,620 B2* | 7/2015 | Shin | ................... | A61B 6/4435 |
| 9,101,328 B2* | 8/2015 | Tsuji | ................. | H01L 27/14605 |
| 9,265,467 B2* | 2/2016 | Kamiya | .............. | A61B 6/548 |
| 9,541,509 B2* | 1/2017 | Akahori | ............. | A61B 6/486 |
| 9,554,759 B2* | 1/2017 | Hawver | ............. | A61B 6/4233 |
| 9,554,762 B2* | 1/2017 | Kim | ................... | A61B 6/5241 |
| 9,610,053 B2* | 4/2017 | Okuno | .............. | A61B 6/486 |
| 9,640,086 B2* | 5/2017 | Van Leer | .......... | G09B 9/003 |
| 9,697,923 B2* | 7/2017 | Tsuji | ................ | G21K 4/00 |
| 9,700,270 B2* | 7/2017 | Tateishi | ............ | A61B 6/4266 |
| 9,820,703 B2* | 11/2017 | Wojcik | .............. | A61B 6/4283 |
| 10,342,508 B2* | 7/2019 | Matsushita | ......... | A61B 6/566 |
| 10,499,863 B2* | 12/2019 | Wojcik | .............. | A61B 6/4283 |
| 10,695,024 B2* | 6/2020 | Miyamoto | .......... | H04N 5/367 |

* cited by examiner

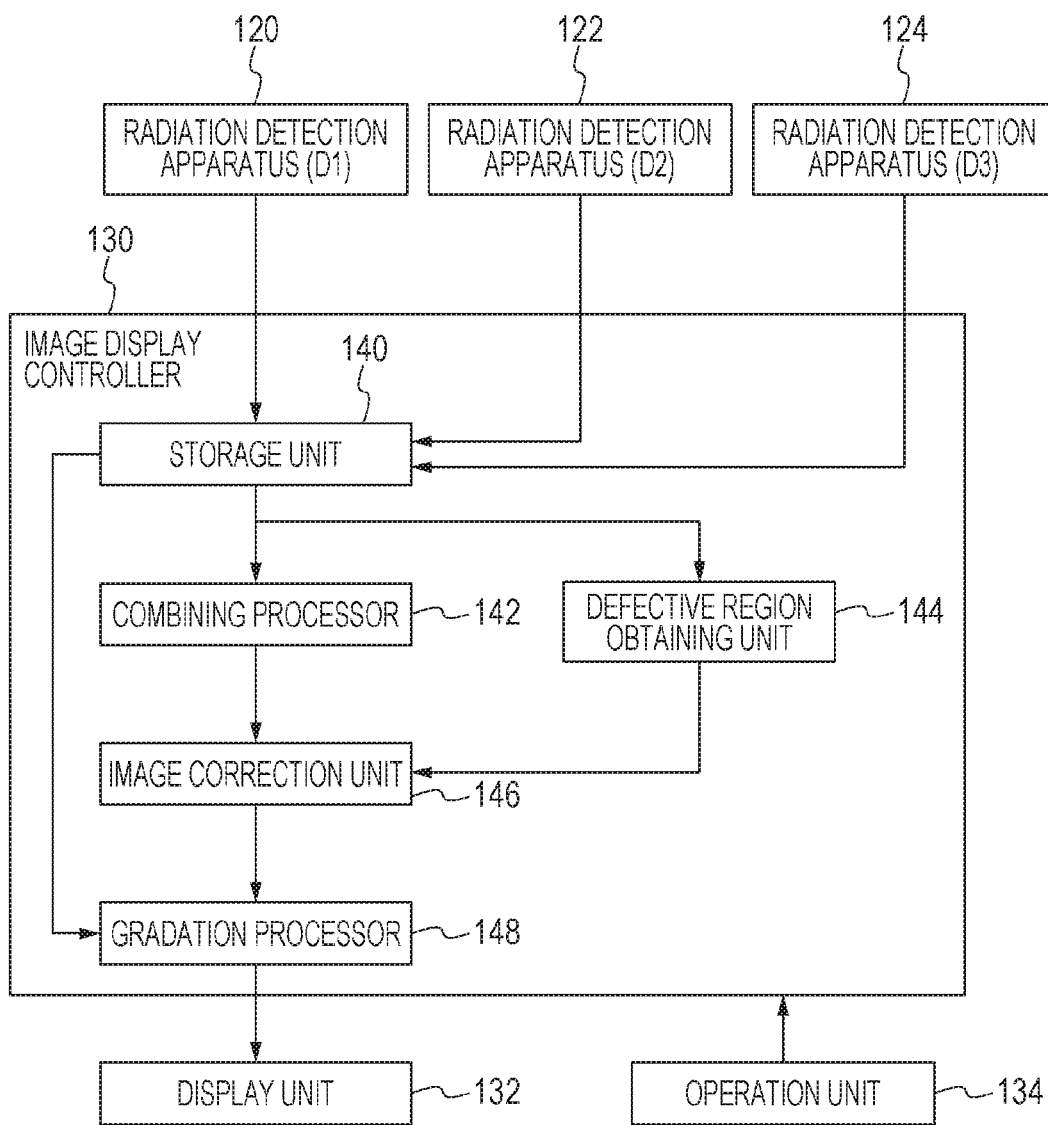

RADIOGRAPHIC SYSTEM AND RADIOGRAPHIC METHOD FOR OBTAINING A LONG-SIZE IMAGE AND CORRECTING A DEFECTIVE REGION IN THE LONG-SIZE IMAGE

CROSS-REFERENCE TO RELATED APPLICATIONS

This application is a Continuation of co-pending U.S. patent application Ser. No. 15/006,619, filed Jan. 26, 2016, which issued as U.S. Pat. No. 10,695,024 B2 on Jun. 30, 2020 and which claims foreign priority benefit of Japanese Patent Application No. 2015-017890, filed Jan. 30, 2015. The disclosures of the above-named applications are hereby incorporated by reference herein in their entirety.

BACKGROUND OF THE INVENTION

Field of the Invention

The present invention relates to a radiographic system which performs imaging using radial rays and a radiographic method.

Description of the Related Art

In recent years, imaging of a large observing region (hereinafter referred to as "long-size imaging") is performed for imaging of a spinal cord, entire lower extremities, or a whole body of an object, for example, in a medical field. Japanese Patent Laid-Open No. 2012-040140 discloses a radiographic system capable of performing the long-size imaging by performing imaging using a plurality of arranged radiation detection apparatuses (radiographic apparatuses).

In Japanese Patent Laid-Open No. 2012-040140, when imaging is performed using the plurality of arranged radiation detection apparatuses while portions of adjacent two of the radiation detection apparatuses overlap with each other, in each pair of the radiation detection apparatuses, a portion of one of the radiation detection apparatuses which is located nearer to a radiation generation unit is included in an image obtained by the other of the radiation detection apparatuses which is located further from the radiation generation unit. Specifically, a radiation image output from one of the radiation detection apparatuses includes a structure of the other of the radiation detection apparatuses. The structure of the radiation detection apparatus is nothing to do with the object that is a diagnosis target, and therefore, a portion in the image corresponding to the structure is a defective region. The defective region remains even when a long-size image (a composite image) is obtained by combining a plurality of radiation images with each other. However, Japanese Patent Laid-Open No. 2012-040140 does not refer to a countermeasure for such an unexpected image.

SUMMARY OF THE INVENTION

According to the present invention, there is provided a radiographic system and a radiographic method which improve quality of a long-size image including a defective region caused by a structure of a radiation detection apparatus. The radiographic system including a plurality of radiation detection apparatuses which detect radial rays and a combining processor which generates a long-size image by combining a plurality of radiation images obtained from the radiation detection apparatuses further includes an image correction unit which corrects the defective region in which the radiation detection apparatuses overlap with each other in the long-size image.

Further features of the present invention will become apparent from the following description of exemplary embodiments with reference to the attached drawings.

BRIEF DESCRIPTION OF THE DRAWINGS

FIG. 9 is a diagram illustrating a configuration of a radiographic system according to a third embodiment.

DESCRIPTION OF THE EMBODIMENTS

Hereinafter, preferred embodiments of the present invention will be described with reference to the accompanying drawings.

First Embodiment

Figure 1:
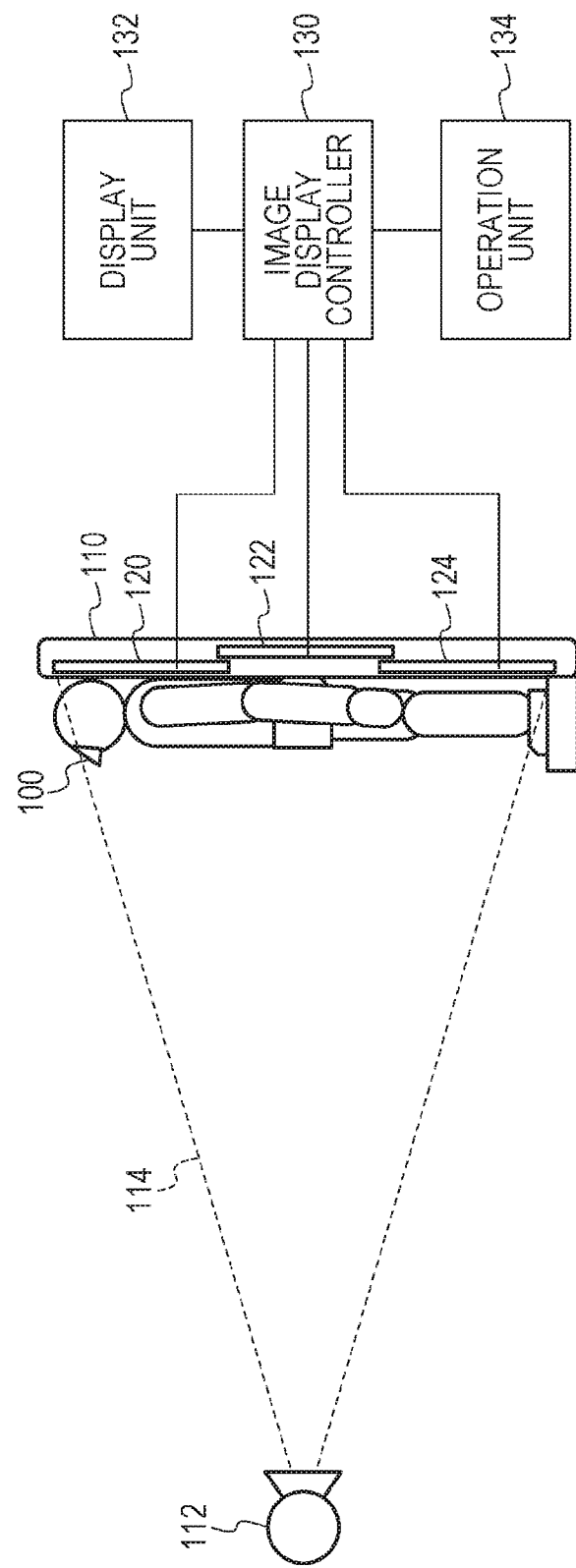
FIG. 1 is a diagram schematically illustrating a configuration of a radiographic system according to a first embodiment.

FIG. 1 is a diagram schematically illustrating a configuration of a radiographic system according to a first embodiment. Specifically, FIG. 1 is a diagram schematically illustrating a configuration of a radiographic system used for long-size imaging performed using a plurality of radiation detection apparatuses which are arranged.

The radiographic system includes a radiation generation unit 112 which generates radial rays. The radiation generation unit 112 may output radial rays in the irradiation range 114. The radiation generation unit 112 is disposed through a supporting unit (not illustrated) installed on a floor surface or a ceiling. A diaphragm (not illustrated) which shields radial rays is disposed on an irradiation surface of the radiation generation unit 112. An operator controls the diaphragm which shields radial rays so as to set the irradiation range 114 of radial rays emitted from the radiation generation unit 112.

The radiographic system includes a plurality of radiation detection apparatuses 120, 122, and 124. Although the three radiation detection apparatuses 120, 122, and 124 are illustrated in this embodiment, two radiation detection apparatuses or four or more radiation detection apparatuses may be provided. The radiation detection apparatuses 120, 122, and 124 detect radial rays which pass through an object 100 and output image data corresponding to the radial rays. The "image data" may be replaced by a "radiation image".

Specifically, the radiation detection apparatuses 120, 122, and 124 detect radial rays which are transmitted through the object 100 as charges corresponding to transmitted radiation amounts. For example, as the radiation detection apparatuses 120, 122, and 124, an a-Se direct conversion sensor which directly converts radial rays into charge or an indirect sensor using a CsI scintillator and an a-Si photoelectric conversion device is used. Furthermore, the radiation detection apparatuses 120, 122, and 124 generate image data by performing A/D conversion on the detected charges and output the image data to an image display controller 130.

The radiation detection apparatuses 120, 122, and 124 are accommodated in a radiographic stand 110. The radiographic stand 110 is a rectangular hollow casing. Furthermore, the radiographic stand 110 has a function of holding the radiation detection apparatuses 120, 122, and 124.

As illustrated in FIG. 1, the radiographic stand 110 is disposed perpendicular to the floor surface. The object 100 is positioned along a longitudinal direction of the radiographic stand 110. The radiographic stand 110 has a function of supporting the object 100.

In FIG. 1, the radiographic stand 110 is disposed such that the longitudinal direction of the radiographic stand 110 corresponds to a vertical direction, that is, the radiographic stand 110 stands erect relative to the floor surface. Note that the radiographic stand 110 may be disposed such that the longitudinal direction of the radiographic stand 110 corresponds to a horizontal direction, that is, the radiographic stand 110 may be disposed in parallel to the floor surface.

The radiation detection apparatuses 120, 122, and 124 are arranged in the radiographic stand 110 along the longitudinal direction of the radiographic stand 110. Here, the radiation detection apparatuses 120, 122, and 124 are arranged while portions of adjacent two of the radiation detection apparatuses 120, 122, and 124 overlap with each other. As illustrated in FIG. 1, for example, the radiation detection apparatuses 120 and 122 are arranged such that portions of the radiation detection apparatuses 120 and 122 spatially overlap with each other. Here, imaging available regions of the radiation detection apparatuses 120 and 122 overlap with each other. Similarly, the radiation detection apparatuses 122 and 124 are arranged such that portions of the radiation detection apparatuses 122 and 124 spatially overlap with each other. Here, imaging available regions of the radiation detection apparatuses 122 and 124 overlap with each other. Furthermore, the radiation detection apparatus 122 is disposed in a position on back sides of the radiation detection apparatuses 120 and 124, that is, a position far from the radiation generation unit 112.

Furthermore, the radiographic system includes the image display controller 130 which performs image processing on image data output from the radiation detection apparatuses 120, 122, and 124 so as to generate an image, a display unit 132 which displays the image, and an operation unit 134 used by the operator to issue an instruction. The image display controller 130 has a function of controlling the components. The image display controller 130 includes a CPU, a memory, and a hard disk. The image display controller 130 performs control using the CPU.

The image display controller 130 is connected to the radiation detection apparatuses 120, 122, and 124. Specifically, the image display controller 130 is connected to the radiation detection apparatuses 120, 122, and 124 by a wired network, a wireless network, a wired dedicated line, or a wireless dedicated line. The radiation detection apparatuses 120, 122, and 124 image radial rays generated by the radiation generation unit 112 and output image data to the image display controller 130. The image display controller 130 has an application function operating in a computer. The image display controller 130 outputs an image to the display unit 132 and outputs graphical user interfaces while controlling the operations of the radiation detection apparatuses 120, 122, and 124.

The image display controller 130 controls a timing when the radiation generation unit 112 generates radial rays and a condition for imaging radial rays. Furthermore, the image display controller 130 controls a timing when image data of the radiation detection apparatuses 120, 122, and 124 is captured and a timing when the image data of the radiation detection apparatuses 120, 122, and 124 is output. The image display controller 130 causes the radiation detection apparatuses 120, 122, and 124 to simultaneously perform imaging and to simultaneously output image data.

The image display controller 130 has a function of performing image processing, such as noise reduction, on the image data output from the radiation detection apparatuses 120, 122, and 124. The image display controller 130 may further perform image processing, such as trimming or rotation, on the image data output from the radiation detection apparatuses 120, 122, and 124. The display unit 132 displays the image output from the image display controller 130.

The object 100 stands on a step disposed on the radiographic stand 110 so as to be positioned relative to the radiation detection apparatuses 120, 122, and 124 and the radiation generation unit 112. In this embodiment, radial rays are emitted at an angle in which the radial rays are perpendicularly incident on a center of the radiation detection apparatus 122. The radial rays emitted from the radiation generation unit 112 to the radiation detection apparatuses 120, 122, and 124 are transmitted through the object 100 and reach the radiation detection apparatuses 120, 122, and 124 which detect the radial rays. The image data obtained by the radiation detection apparatuses 120, 122, and 124 is subjected to a combining process in the image display controller 130 so that a composite image of the object 100 is generated. The composite image is a long-size image having a large observing region obtained by long-size imaging. The display unit 132 displays the long-size image output from the image display controller 130.

In the radiographic system of the present invention, long-size imaging in which a spinal cord, entire lower extremities, or a whole body of the object 100 is captured may be performed by one radial ray irradiation. The radiation generation unit 112 simultaneously emits radial rays (in the irradiation range 114) to the radiation detection apparatuses 120, 122, and 124. The operator controls the diaphragm which shields radial rays and controls distances between the radiation detection apparatuses 120, 122, and 124 and the radiation generation unit 112, for example.

The radiation detection apparatuses 120, 122, and 124 may have a detection function of automatically detecting emission of radial rays from the radiation generation unit 112. By the automatic detection function, the radiation detection apparatuses 120, 122, and 124 detect radial rays which are emitted from the radiation generation unit 112 and store charges caused by the radial rays. When emission of radial rays is detected by one of the radiation detection apparatuses 120, 122, and 124, the radiation detection apparatuses 120, 122, and 124 start a real read operation so as to obtain image data.

Figure 2:
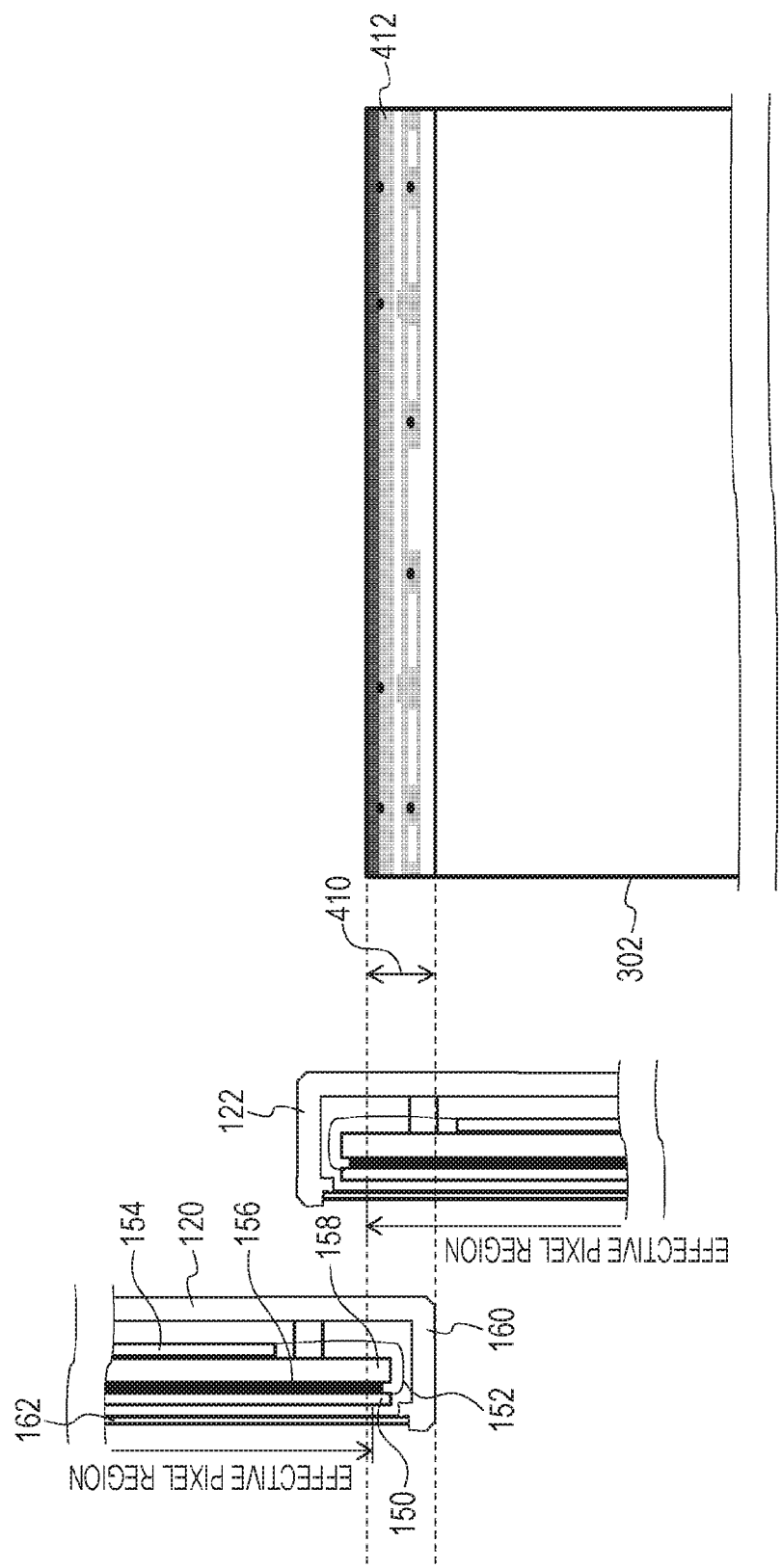
FIG. 2 is a diagram illustrating the relationship between radiation detection apparatuses of the radiographic system according to the first embodiment and image data.

In the radiographic system described above, the radiation detection apparatus 122 is disposed so as to overlap with the radiation detection apparatuses 120 and 124 on the back sides of the radiation detection apparatuses 120 and 124. Therefore, the image data output from the radiation detection apparatus 122 includes defective regions including images of structures (structure information), such as radiation detection panels, substrates, and, cases, which are internal components of the radiation detection apparatuses 120 and 124. To describe such a defective region, the relationship between the radiation detection apparatuses 120 and 122 in the radiographic system of the present invention and a radiation image will be described with reference to FIG. 2.

The radiation detection apparatus 120 includes a junction body obtained by laminating, from a radiation input surface side, a radiation detection panel 150 which detects radial rays, a pressure-sensitive member 156 which causes the radiation detection panel 150 to adhere to a panel base 158, the panel base 158 which supports the radiation detection panel 150, and a control substrate 154 which causes the radiation detection panel 150 to output an electric signal. The radiation detection panel 150 and the control substrate 154 are connected to each other through a flexible substrate 152.

An outer casing of the radiation detection apparatus 120 is constituted by a metallic case 160 and a radiation transmission unit 162 formed of a radiation transmission member which allows radial rays to be transmitted. The radiation transmission unit 162 is disposed on a radiation input surface of the radiation detection panel 150 so as to suppress attenuation of radial rays emitted from the radiation generation unit 112. The radiation detection panel 150 includes an effective pixel region in which radial rays may be detected and a peripheral portion in an outer periphery of the effective pixel region.

Although a description is omitted, the radiation detection apparatuses 122 and 124 have configurations the same as that of the radiation detection apparatus 120.

The radiation detection apparatus 122 has an effective pixel region which overlaps with a portion of the effective pixel region of the radiation detection apparatus 120, and at least one of the effective pixel regions of the radiation detection apparatuses 120 and 122 reliably obtains image information in any line. A long-size image is generated from the image data (the radiation image) output from the radiation detection apparatus 120 and image data (a radiation image) of an image region which has not been obtained by the radiation detection apparatus 120 in the image data output from the radiation detection apparatus 122.

Here, an image of the structure included in the radiation detection apparatus 120 is included in image data 302 obtained by the radiation detection apparatus 122. In a region 410 in a range from an end portion of the effective pixel region of the radiation detection apparatus 122 to an end portion of the outer casing of the radiation detection apparatus 120, an image of the structure of the radiation detection apparatus 120 is included in an image obtained by the radiation detection apparatus 122. Therefore, a defective region 412 is generated owing to the unexpected image of the structure of the radiation detection apparatus 120 in the image data 302 obtained by the radiation detection apparatus 122. Accordingly, the defective region 412 is also generated in a long-size image generated by a combining processor 142 from the image data 302 obtained by the radiation detection apparatus 122.

Information on an image including a portion of the radiation detection panel 150, a portion of the flexible substrate 152, a portion of the pressure-sensitive member 156, a portion of the panel base 158, and a portion of the metallic case 160 included in the radiation detection apparatus 120 is included in the defective region 412 of the image data 302 obtained by the radiation detection apparatus 122. Furthermore, information on an image of a substrate on the flexible substrate 152 and information on an image of screws and the like are also included in the defective region 412.

Although not illustrated, a defective region is generated owing to an unexpected image of the structure of the radiation detection apparatus 124 in the image data 302 obtained by the radiation detection apparatus 122.

As described hereinabove, the defective region is a defect of image information caused by a structure having low radiation transmittance, and object information is lost in the defective region. Accordingly, the defective region may prevent diagnosis using a long-size image.

Figure 3:
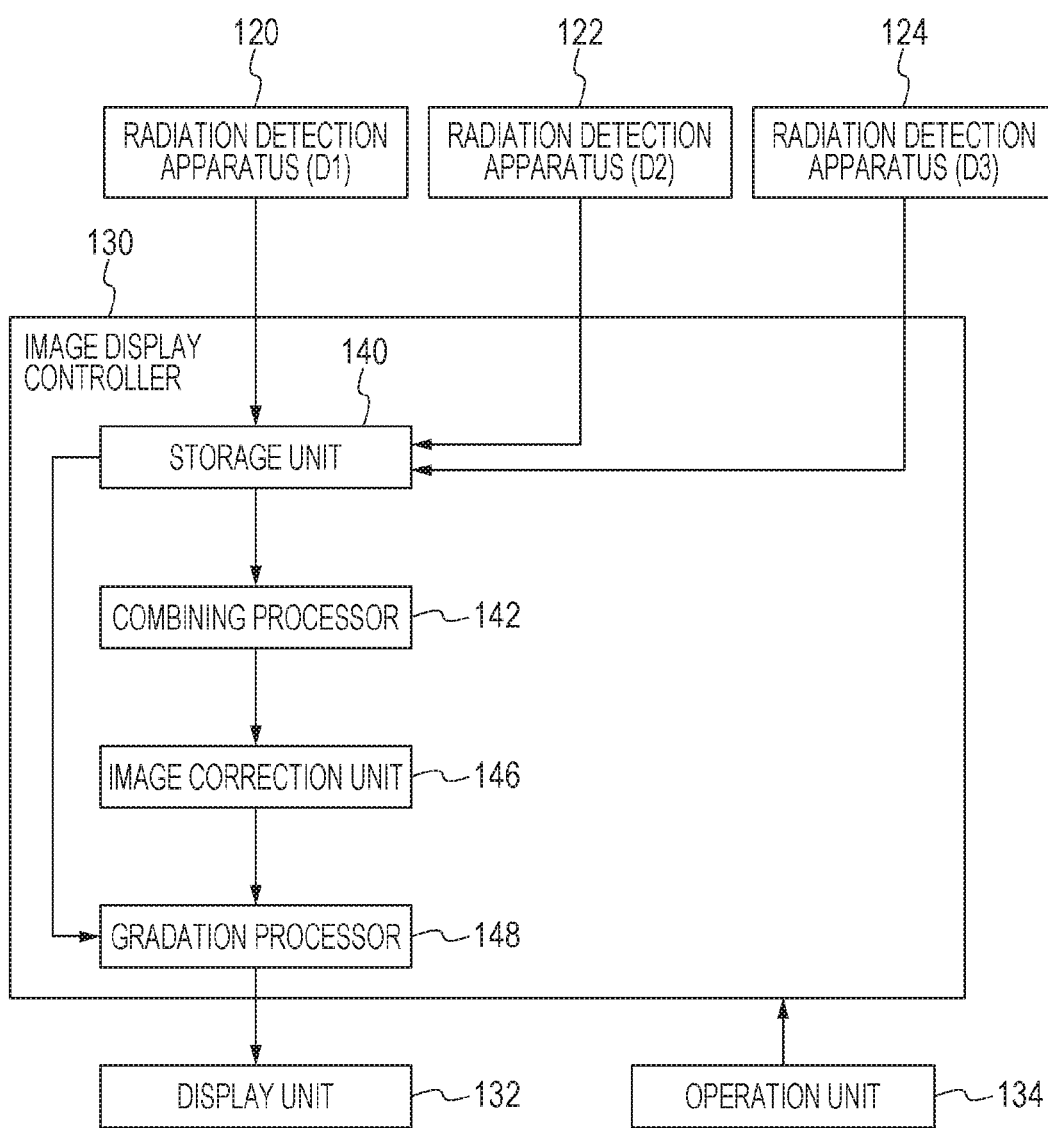
FIG. 3 is a diagram illustrating a configuration of the radiographic system (mainly, an image display controller) according to the first embodiment.

Next, a mode for reducing defective regions of a long-size image generated by overlap between the radiation detection apparatuses described above so that image quality is improved will be described with reference to a configuration of the radiographic system according to the present invention in FIG. 3.

The image display controller 130 includes a storage unit 140 which stores image data output from the radiation detection apparatuses 120, 122, and 124, the combining processor 142 which generates a long-size image by combining the image data, an image correction unit 146 which corrects defective regions generated in the long-size image so that defects are reduced, and a gradation processor 148 which performs a gradation process on the long-size image corrected by the image correction unit 146.

The storage unit 140 stores the image data (the radiation images) output from the radiation detection apparatuses 120, 122, and 124. As illustrated in FIG. 3, the radiation detection apparatuses 120, 122, and 124 are represented as radiation detection apparatuses (D1), (D2), and (D3), respectively.

The storage unit 140 may store the image data output from the radiation detection apparatuses 120, 122, and 124 with time information. Therefore, the storage unit 140 may store the radiation images output from the radiation detection apparatuses 120, 122, and 124 while determining whether the radiation images are simultaneously obtained in accordance with the information on times when the radiation images are obtained. The storage unit 140 may store the radiation images after determining whether each of the radiation images includes information on an image of the object 100.

Furthermore, the storage unit 140 may store the radiation images simultaneously obtained by the radiation detection apparatuses 120, 122, and 124 associated with positional information (spatial location information) of the radiation detection apparatuses 120, 122, and 124. For example, the storage unit 140 may store information indicating that the image data output from the radiation detection apparatus 120 and the image data output from the radiation detection apparatus 122 are adjacent to each other which is associated with the radiation images. Similarly, the storage unit 140 may store information indicating that the image data output from the radiation detection apparatus 122 and the image data output from the radiation detection apparatus 124 are adjacent to each other which is associated with the radiation images. Furthermore, the storage unit 140 may store information indicating that the radiation detection apparatus 122 is disposed on the back sides of the radiation detection apparatuses 120 and 124 which is associated with the radiation images. The storage unit 140 may output the plurality of image data and the positional information thereof to the combining processor 142.

The combining processor 142 combines the plurality of image data stored in the storage unit 140 so as to generate a long-size image. Here, the combining processor 142 combines the plurality of image data including the image information on the object 100 so as to generate a long-size image.

The combining processor 142 performs the combining in accordance with the plurality of image data output from the radiation detection apparatuses 120, 122, and 124, the time information thereof, and the positional information thereof so as to generate a long-size image. Specifically, the combining processor 142 determines that the plurality of image data (the radiation images) simultaneously output from the radiation detection apparatuses 120, 122, and 124 is to be combined in accordance with the time information and combines the plurality of image data. The combining processor 142 determines positional relationships among the plurality of image data output from the radiation detection apparatuses 120, 122, and 124 in accordance with the positional information before the combining process.

In the example of FIG. 1, the image data output from the radiation detection apparatus 120 is positioned in an upper portion, the image data output from the radiation detection apparatus 124 is positioned in a lower portion, and the image data output from the radiation detection apparatus 122 is positioned between the upper and lower portions. Furthermore, the combining process is performed taking overlap represented by the positional information into consideration. For example, defective regions are generated in upper and lower portions of the image data 302 obtained by the radiation detection apparatus 122 disposed in a position far from the radiation generation unit 112 so as to overlap with the other radiation detection apparatuses 120 and 124. However, a defective region is not generated in image data obtained by the radiation detection apparatuses 120 and 124. Therefore, the combining processor 142 generates a long-size image using the image data generated by the radiation detection apparatuses 120 and 124 in regions in which the radiation detection apparatus 122 and the radiation detection apparatuses 120 and 124 overlap with each other so as to minimize areas of the defective regions generated in the long-size image. In this way, the combining processor 142 combines the plurality of image data obtained by capturing a plurality of imaging regions which are adjacent to each other so as to generate a long-size image.

The image correction unit 146 performs a process of correcting the composite image output from the combining processor 142 so that the defective regions are reduced. The image correction unit 146 corrects the defective regions including the images of the structures of the radiation detection apparatuses 120 and 124 using pixel values included in pixel regions other than the defective regions. Specifically, the image correction unit 146 performs the correction using structure information indicating the structures of the radiation detection apparatuses 120 and 124 and pixel value distributions in normal regions which are adjacent to the defective regions. In other words, the image correction unit 146 corrects the defective regions of the long-size image using the information on the normal image regions which are adjacent to the defective regions.

Here, the structure information is information on a structure of a radiation detection apparatus which may be included in a radiation image. The structure information includes information on a radiation attenuation coefficient, a thickness, a position, and the like of a substance included in the radiation detection apparatus. In a case where a defective region in a long-size image is to be corrected, it is expected that an end of the defective region has correlation with a pixel value distribution of a normal region which is spatially adjacent to the defective region if an unexpected image of a structure is not included. Accordingly, taking information on the structure of the unexpected image into consideration, the image correction unit 146 performs correction such that a pixel value distribution of a defective region becomes similar to that of a normal region so as to reduce the defective region.

Here, to simplify a description, a method for using data on an image captured by overlapping a plurality of radiation detection apparatuses with each other without an object as structure information will be described. In the structure information, an unexpected image of a structure of a radiation detection apparatus is represented as a pixel value. A pixel corresponding to an unexpected image of a structure having a large thickness and a large radiation attenuation coefficient has a small pixel value whereas a pixel corresponding to an unexpected image of a structure having a small thickness and a small radiation attenuation coefficient has a large pixel value.

Figure 4:
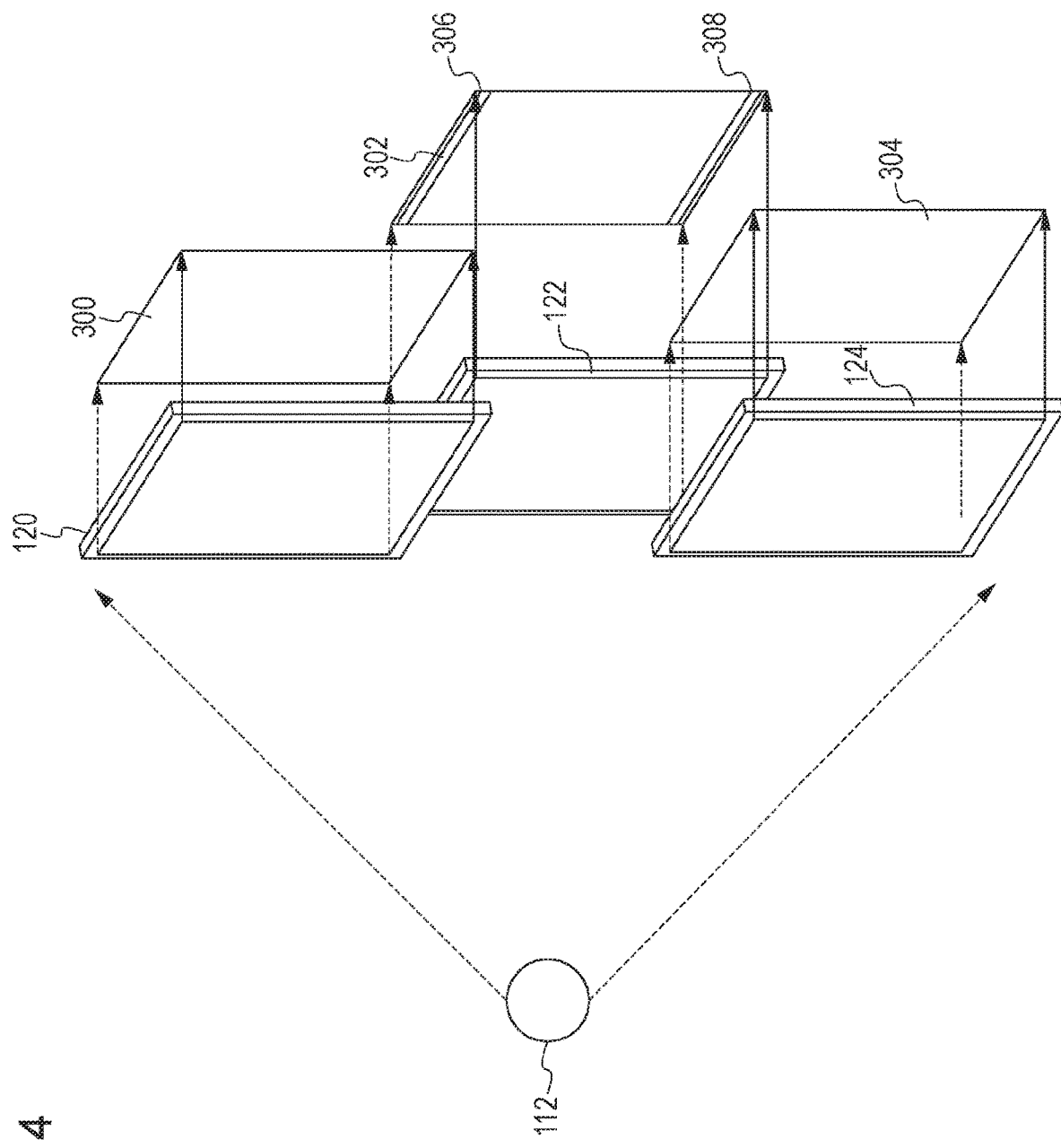
FIG. 4 is a diagram illustrating defective regions in a long-size image in the radiographic system according to the first embodiment.

A case where structure information is included in image data will be described with reference to FIG. 4. FIG. 4 is a diagram schematically illustrating a form of the configuration of the radiographic system and the image data (including defective regions). In a case where the radiation detection apparatuses 120, 122, and 124 are arranged in the form illustrated in FIG. 4 and imaging is performed without an object, the structure information of the radiation detection apparatuses 120 and 124 is included in the image data 302 obtained by the radiation detection apparatus 122.

Specifically, an unexpected image region 306 corresponding to the structure information in a lower portion of the radiation detection apparatus 120 which overlaps with the radiation detection apparatus 122 is included in the image data 302 obtained by the radiation detection apparatus 122. Furthermore, an unexpected image region 308 corresponding to the structure information in an upper portion of the radiation detection apparatus 124 which overlaps with the radiation detection apparatus 122 is included in the image data 302 obtained by the radiation detection apparatus 122.

Note that image data (a radiation image) 300 obtained by the radiation detection apparatus 120 does not include an unexpected image of structure information of another radiation detection apparatus. Furthermore, image data (a radiation image) 304 obtained by the radiation detection apparatus 124 does not include an unexpected image of structure information of another radiation detection apparatus. Therefore, the image data 302 corresponds to structure data having the unexpected images as position-and-pixel-value information. The unexpected image regions 306 and 308 may be seen to be structure information.

Positions of the defect regions in the long-size image may be obtained using the positional information of the radiation detection apparatuses 120, 122, and 124 stored in the storage unit 140 or may be obtained using the structure information. Specifically, if information defects in the long-size image represented by the structure information are detected in the long-size image, regions of the detected information defects correspond to the defect regions. In a case where the unexpected image regions 306 and 308 described above are used as the structure information, the image correction unit 146 performs template matching on the long-size image using the structure information as template images. Then, positions having the highest correlations are detected as the defective regions to be corrected by the image correction unit 146.

Figure 5:
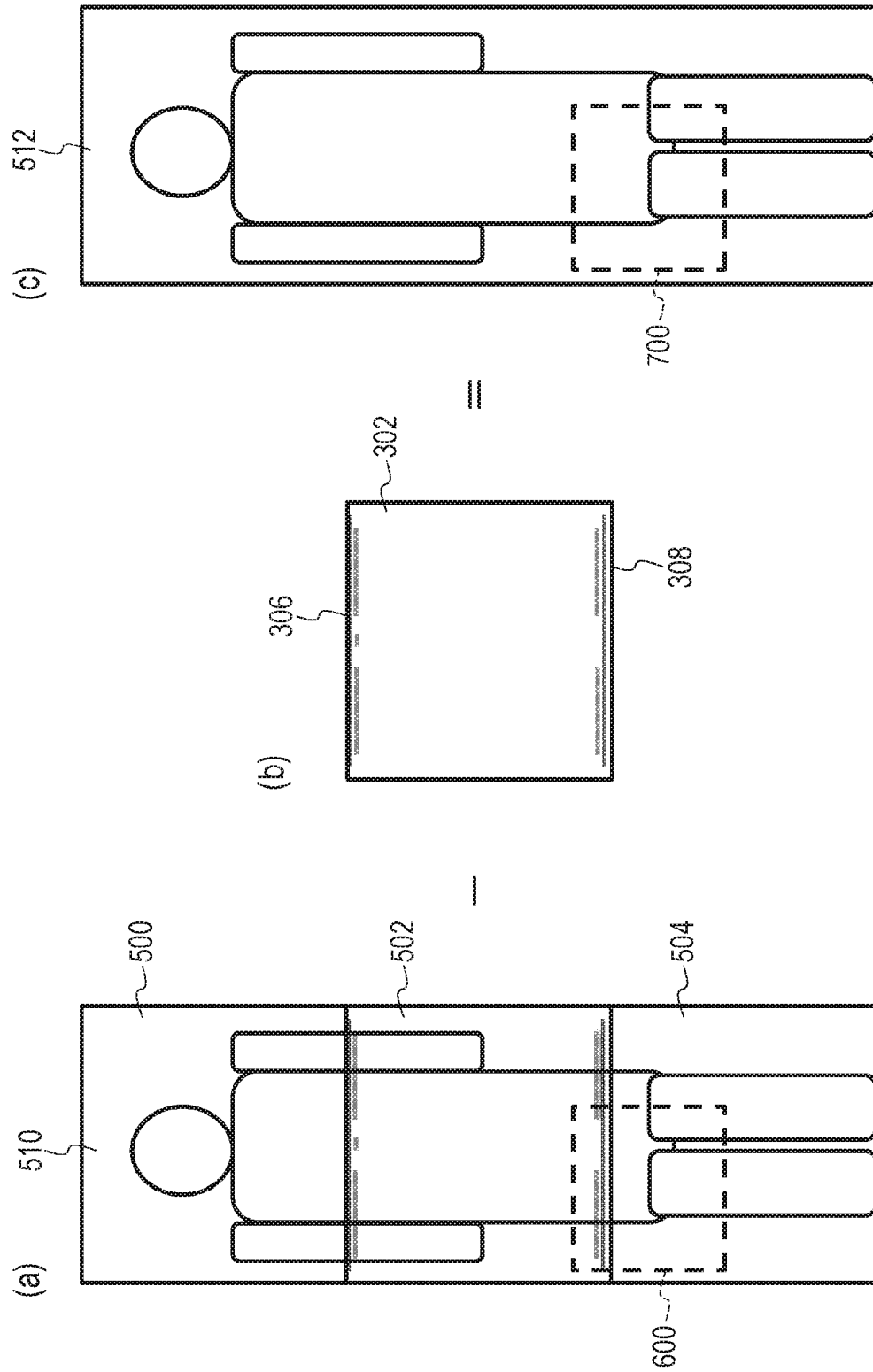
FIG. 5 is a diagram illustrating a correction process performed by an image correction unit included in the radiographic system according to the first embodiment.

FIG. 5 is a diagram illustrating a correction process performed by the image correction unit 146 included in the radiographic system of the present invention. In particular, FIG. 5 is a diagram illustrating a mode in which the defective regions (image defective regions) caused by the unexpected images of the structures of the radiation detection apparatuses 120 and 124 are reduced.

(a) of FIG. 5 is a diagram illustrating a long-size image 510 generated by combining a plurality of image data (radiation images) by the combining processor 142. The long-size image 510 is generated by the combining processor 142 and output to the image correction unit 146.

(b) of FIG. 5 is a diagram illustrating structure information to be used for the correction process performed by the image correction unit 146. Here, imaging is performed without the object 100 and image data obtained by the radiation detection apparatus 122 is determined as the image data 302.

(c) of FIG. 5 is a diagram illustrating a long-size image 512 obtained by correcting the defective regions including the images of the structures of the radiation detection apparatuses 120 and 124 in the long-size image 510 of (a) of FIG. 5. The corrected long-size image 512 is output from the image correction unit 146. Furthermore, an image 500 illustrated in (a) of FIG. 5 corresponds to the image data output from the radiation detection apparatus 120, and in this example, a head and shoulders of the object 100 are mainly included. Subsequently, an image 502 illustrated in (a) of FIG. 5 corresponds to the image data output from the radiation detection apparatus 122, and in this example, a trunk and arms of the object 100 are mainly included. The structure information of the radiation detection apparatuses 120 and 124 is included in an upper end portion and a lower end portion of the image 502, respectively, that is, defective regions are generated. The combining processor 142 performs the combining process in accordance with the layout relationship among the radiation detection apparatuses 120, 122, and 124 such that areas of the defective regions in the image 510 are minimized.

An image 504 illustrated in (a) of FIG. 5 corresponds to the image data output from the radiation detection apparatus 124, and in this example, legs of the object 100 are mainly included.

As illustrated in (a) of FIG. 5, the combining processor 142 combines the images 500, 502, and 504 so as to generate the long-size image 510. In this way, a whole-body image of the object 100 is obtained.

As illustrated in (c) of FIG. 5, the image correction unit 146 performs the correction process on the long-size image 510 illustrated in (a) of FIG. 5 so that the defective regions generated due to the unexpected images of the structures of the radiation detection apparatuses 120 and 124 are reduced. Specifically, the image correction unit 146 generates the long-size image 512 by correcting the defective regions including the unexpected images of the portions of the radiation detection apparatuses 120 and 124 (the structures of the radiation detection apparatuses 120 and 124).

Figure 6:
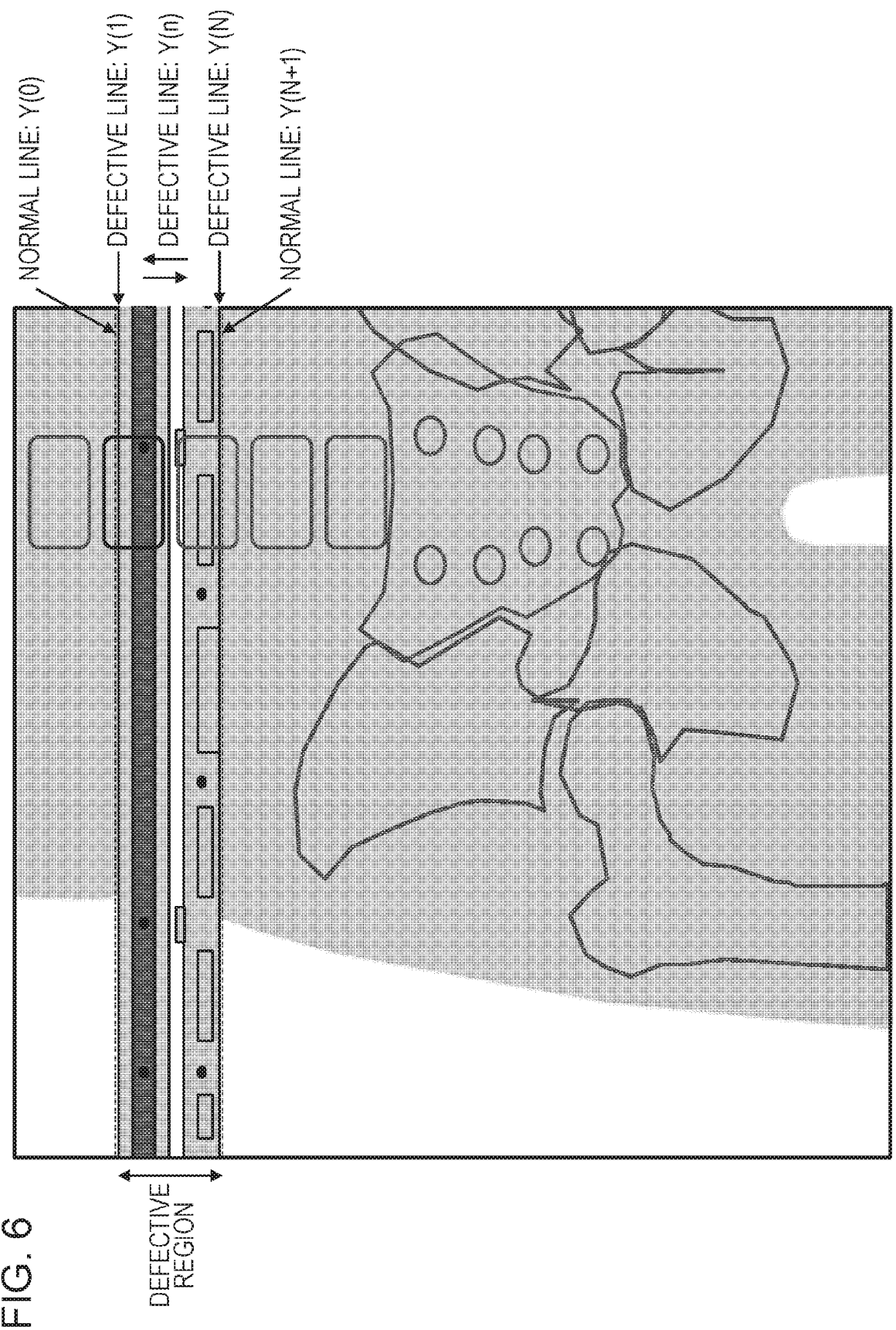
FIG. 6 is a diagram illustrating the correction process performed by the image correction unit included in the radiographic system according to the first embodiment.
Figure 7:
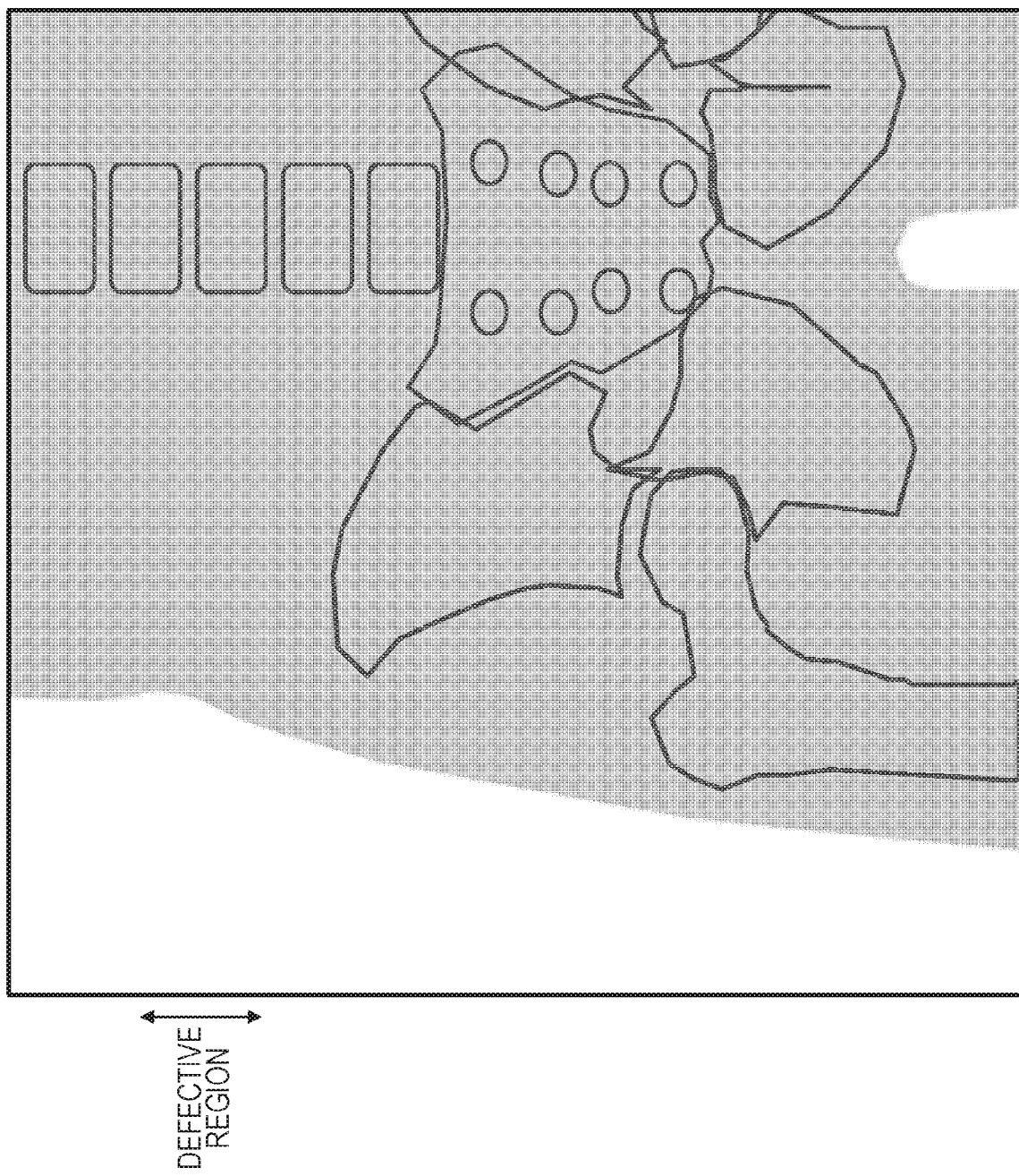
FIG. 7 is a diagram illustrating the correction process performed by the image correction unit included in the radiographic system according to the first embodiment.

The correction process performed by the image correction unit 146 is now illustrated with reference to FIGS. 6 and 7. FIG. 6 is an enlarged view of a region 600 denoted by a dotted line in FIG. 5, and FIG. 7 is an enlarged view of a region 700 denoted by a dotted line in FIG. 5.

The image correction unit 146 corrects defective lines included in the defective region of the long-size image 510 using normal lines which include normal image regions and which are adjacent to the defective lines. The image correction unit 146 mixes radiation images of the normal lines with radiation images of the defective lines while the correlations therebetween are ensured so as to correct the defective lines. The image correction unit 146 performs positioning between the defective region in the long-size image 510 and the structure information and corrects the long-size image 510 using defective information included in the structure information corresponding to the defective lines included in the long-size image 510.

A range of the defective region to be corrected by the image correction unit 146 is specified by line numbers from Y(1) to Y(N) in the long-size image 510 as illustrated in FIG. 6. A line Y(n) (1≤n≤N) included in the defective region is referred to as a defective line. Here, lines Y(0) and Y(N+1) which are located adjacent to the lines Y(1) and Y(N), respectively, which are terminal end lines of the defective region are referred to as "normal lines".

The image correction unit 146 corrects the defective lines one by one using the normal lines which are located adjacent to the defective lines. A corrected defective line newly becomes a normal line to be used for correction of a next defective line. The process of correcting a defective line to a normal line for each defective line is repeatedly performed so that the entire defective region is processed. In this way, the correction is performed. Specifically, the image correction unit 146 divides a defective region included in a long-size image into defective lines in a unit of line and repeatedly performs, on the individual defective lines, a process of approximating, from an end line of the defective region, a pixel value distribution of one of the defective lines to that of a normal line which is included in a normal region adjacent to the end line or a corrected defective line.

For example, in a case where the correction is performed downward on the image, the defective line Y(1) is corrected using the normal line Y(0). The defective line Y(2) is corrected using the corrected defective line Y(1) which has been converted into a normal line. Accordingly, correction of the defective lines Y(n) in a range in which n is equal to or larger than 1 and equal to or smaller than N may be successively performed using a line Y(n−1) as a normal line. When the correction is performed upward, the defective lines Y(n) may be successively corrected using a line Y(n+1) as a normal line starting from the defective line Y(N).

The correction process may be performed herein by any method as long as the method utilizes the correlation between adjacent pixels. It is assumed that x-th pixel (1≤x≤W) in the line Y(n) in the long-size image is denoted by a coordinate (x, Y, (n)), and a pixel value in the coordinate before the correction is denoted by I(x, Y, (n)). A pixel value after the correction is denoted by O(x, Y(n)) as represented by the following expression.

$$O(x, Y(n)) = f(I(x, Y(n)))$$

In the expression above, the function f minimizes the following expression.

$$E = \frac{1}{2} \sum_{x=1}^{W} \{I(x, Y(m)) - f(I(x, Y(n)))\}^2 \qquad \text{Expression 1}$$

In the expression above, "Y(m)" denotes a normal line which is adjacent to the line Y(n). For example, the function f is represented by a polynomial and a polynomial coefficient is obtained by a least-square method so that a function of converting a defective line into a normal line may be obtained for each line. The correction may be performed by calculating Expression 1 using this function.

Furthermore, the correction may be performed additionally using the structure data. It is assumed that a pixel value in the structure data corresponding to the coordinate (x, Y(n)) is represented by P(x, Y(n)). It is further assumed that the pixel value P(x, Y(n)) in the structure data has information on the structure of the radiation detection apparatus 124 included in a pixel value I(x, Y(n)) of the long-size image. Here, the pixel value O(x, Y(n)) in the coordinate obtained after the correction is represented by the following expression.

$$O(x, Y(n)) = g(I(x, Y(n)), P(x, Y(n)))$$

In the expression above, the function g minimize the following expression.

$$E = \frac{1}{2} \sum_{x=1}^{w} \{I(x, Y(m)) - g(I(x, Y(n)), P(x, Y(n)))\}^2 \quad \text{Expression 2}$$

In the expression above, "Y(m)" denotes a normal line which is adjacent to the line Y(n). For example, the function g is represented by a polynomial and a polynomial coefficient is obtained by a least-square method so that a function of converting a defective line into a normal line may be obtained for each line. Use of the function g enables appropriate correction since the function g performs correction additionally using information on the structure data.

Note that, although the image correction unit 146 may use only a result of correction performed in one direction, results of correction performed in both directions, that is, an upward direction and a downward direction, may be mixed. The image correction unit 146 generates two correction results by performing the bidirectional correction starting from lines which are vertically adjacent to the defective region in the long-size image 510 so as to correct the long-size image 510. The image correction unit 146 generates two image data items, that is, image data of the defective region corrected downward and image data of the defective region corrected upward, for example. The defective line which has been corrected upward and downward is an identical line in the defective region (an overlapping region). Specifically, the image correction unit 146 averages image data of the defective line corrected downward and image data of the defective line corrected upward so as to correct the image data of the defective line. Furthermore, as the corrected defective line is located closer to a normal line which is adjacent to the terminal end of the defective region, correction accuracy of the corrected defective line is seen to be higher. Accordingly, correction results may be mixed taking a weight based on a distance from a correction starting line into consideration. In this case, assuming that the number of lines in the defective region is denoted by "N−1", a result of the correction performed downward is denoted by "O1", and a result of the correction performed upward is denoted by "O2", a result O(n) of correction in an n-th line may be represented by the following expression.

$$O(x, Y(n)) = \frac{(N - 1 - n)}{N - 1} O1(x, Y(n)) + \frac{n}{N - 1} O2(x, Y(n)) \quad \text{Expression 3}$$

FIG. 7 is a diagram illustrating a portion of the long-size image 512 which has been subjected to the correction and which is displayed in the display unit 132. By correcting the defective region (the overlapping region) in the long-size image 510, an image defect caused by the defective region including the image of the structure of the radiation detection apparatus 124 may be reduced, and accordingly, quality of the long-size image 510 may be improved.

The gradation processor 148 performs a gradation process on the long-size image 512 obtained by combining the plurality of image data (the radiation images).

Specifically, the gradation processor 148 obtains the plurality of image data generated by the radiation detection apparatuses 120, 122, and 124 from the storage unit 140. The gradation processor 148 analyzes feature values of the plurality of image data obtained from the radiation detection apparatuses 120, 122, and 124 so as to determine a gradation conversion characteristic of the long-size image 512 so that a dynamic range of the display unit 132 is effectively utilized.

Then the gradation processor 148 converts gradation of the long-size image 512 using the determined gradation conversion characteristic. The feature values include histograms, maximum pixel values, and minimum pixel values of the individual image data, and the feature values are calculated by executing an analysis process on the plurality of image data obtained from the radiation detection apparatuses 120, 122, and 124.

The gradation processor 148 may perform the gradation process on the long-size image 512 corrected by the image correction unit 146. Since the gradation process is performed on the long-size image 512 in which the defective region is reduced in this way, the gradation process may be appropriately performed on the long-size image 512. Specifically, the gradation processor 148 may perform the gradation process on the long-size image 512 while influence of the unexpected images of the structures of the radiation detection apparatuses 120 and 124 is suppressed.

The display unit 132 may display the long-size image 512 in which the defective regions are reduced. Specifically, quality of the long-size image 512 including the unexpected images of the structures of the radiation detection apparatuses 120 and 124 may be improved.

Figure 8:
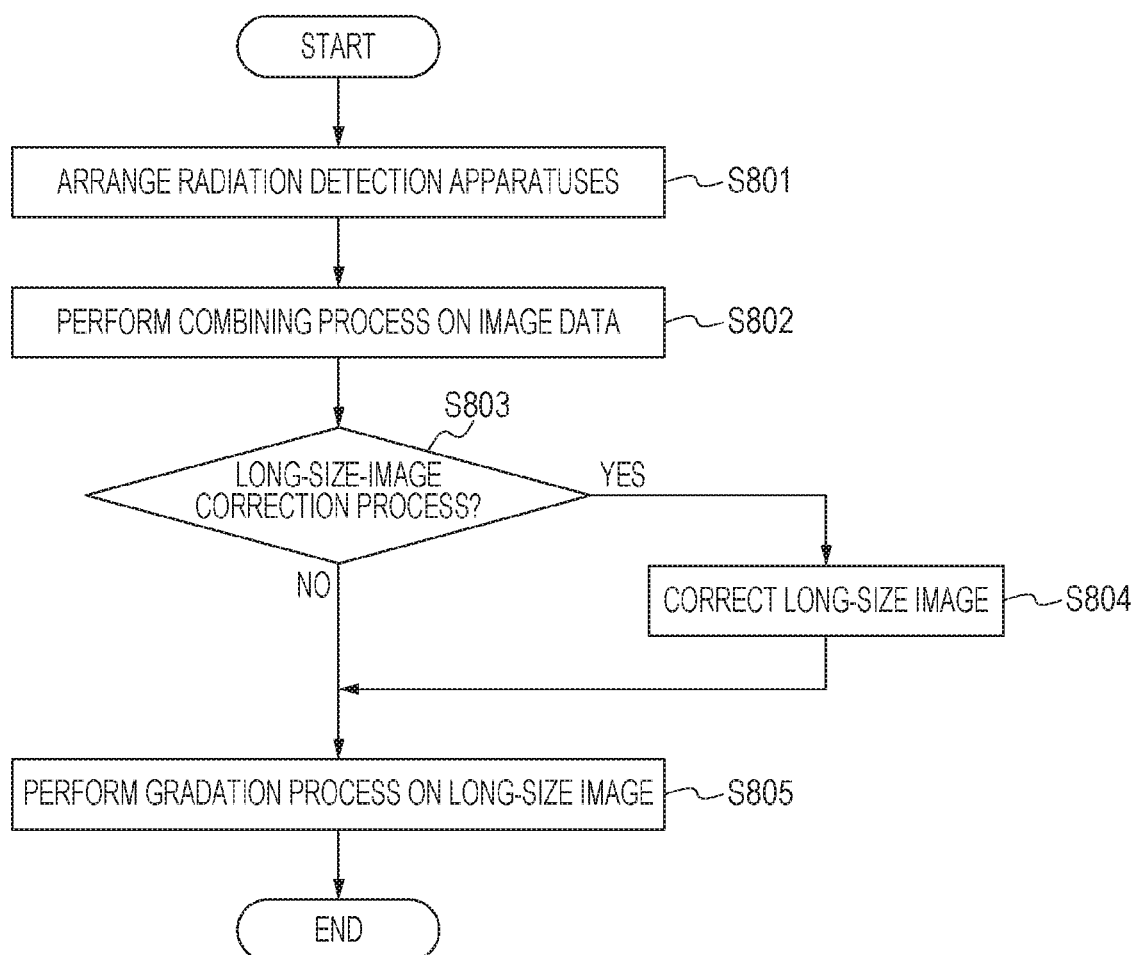
FIG. 8 is a flowchart illustrating operation of the radiographic system according to the first embodiment.

Next, an operation procedure of the radiographic system will be described with reference to a flowchart of FIG. 8.

In step S801, the operator arranges a plurality of radiation detection apparatuses on the radiographic stand 110. That is, the operator arranges the radiation detection apparatuses 120, 122, and 124 on the radiographic stand 110 in a longitudinal direction of the radiographic stand 110. Here, the operator arranges the radiation detection apparatuses 120, 122, and 124 while portions of adjacent two of the radiation detection apparatuses 120, 122, and 124 overlap with each other so that effective pixel regions from which radial rays are detectable overlap with each other.

In step S802, the operator causes the radiation detection apparatuses 120, 122, and 124 to simultaneously perform imaging and to simultaneously output image data to the combining processor 142.

The combining processor 142 combines the image data so as to generate a long-size image.

In step S803, the operator determines whether the correction process is to be performed on the long-size image using the operation unit 134. In a case where the defective regions including the unexpected images of the structures of the radiation detection apparatus 120 and 124 are positioned out of a diagnosis region, for example, the correction process may not be performed. In a case where the correction process is not to be performed on the long-size image, the process proceeds to step S805. In a case where the correction process is to be performed on the long-size image, the process proceeds to step S804.

In step S804, the image correction unit 146 performs a process of reducing the defective regions caused by the unexpected images of the structures of the radiation detection apparatuses 120 and 124 on the long-size image output from the combining processor 142.

In step S805, the gradation processor 148 performs the gradation process on the long-size image output from the combining processor 142. Alternatively, the gradation processor 148 performs the gradation process on the long-size image corrected by the image correction unit 146.

As described hereinabove, according to this embodiment, the radiographic system including the radiation detection apparatuses 120, 122, and 124 which detect radial rays and the combining processor 142 which generates a long-size image by combining a plurality of radiation images obtained from the radiation detection apparatuses 120, 122, and 124 further includes the image correction unit 146 which corrects defective regions in which adjacent two of the radiation detection apparatuses 120, 122, and 124 overlap with each other in the long-size image.

In other words, the radiographic system including the combining processor 142 which generates a long-size image by combining a plurality of radiation images obtained when radial rays are simultaneously emitted through the object to a plurality of radiation detection units in which portions thereof overlap with each other further includes the image correction unit 146 which corrects the defective regions including the unexpected images of the radiation detection units.

The structure information associated with the unexpected images of the radiation detection apparatuses 120 and 124 is used for correction of the defective regions. By this, quality of the long-size image including the defective regions may be improved.

Second Embodiment

A second embodiment will be described. The second embodiment is different from the first embodiment in that a combining processor 142 generates a long-size image by controlling a plurality of image data (radiation images) in accordance with the layout relationship among radiation detection apparatuses.

Specifically, the combining processor 142 generates a long-size image by controlling enlargement factors of the individual image data in accordance with the layout relationship among the radiation detection apparatuses.

A plurality of radiation detection apparatus are arranged on the radiographic stand 110 while portions of adjacent two of the radiation detection apparatuses overlap with each other, and different distances from the radiation detection apparatuses to a radiation generation unit 112 are obtained, and accordingly, different enlargement factors for the object in the image data are used. Specifically, the object 100 is imaged in an enlargement manner in image data obtained by a radiation detection apparatus 122 which is located further than the radiation detection apparatuses 120 and 124 relative to the radiation generation unit 112. Therefore, the combining processor 142 enlarges image data obtained by the radiation detection apparatuses 120 and 124 in accordance with the image data obtained by the radiation detection apparatus 122.

Furthermore, the combining processor 142 may control relative positions of the image data obtained by the radiation detection apparatus 120 and the image data obtained by the radiation detection apparatus 124 in accordance with the image data obtained by the radiation detection apparatus 122. It is likely that a position shift of several millimeters may be generated in arrangement of the radiation detection apparatuses 120, 122, and 124 on a radiographic stand 110 since it is difficult to precisely perform arrangement of radiation detection apparatuses 120, 122, and 124 on the radiographic stand 110 such that relative positions of the image data obtained by the radiation detection apparatuses 120, 122, and 124 are stable. Therefore, the combining processor 142 may perform positioning on the image data, which is obtained by the radiation detection apparatuses 120 and 124 and which is enlarged, in accordance with the image data obtained by the radiation detection apparatus 122 so that the image data is combined.

Note that the combining processor 142 may rotate the image data obtained by the radiation detection apparatuses 120 and 124 in accordance with the image data obtained by the radiation detection apparatus 122. This operation is performed to address the position shift generated when the radiation detection apparatuses 120, 122, and 124 are arranged on the radiographic stand 110.

The enlargement factors, the relative positions, and amounts of the rotation described above may be obtained by performing image analysis on image data included in overlapping regions. For example, a correlation value between the overlapping regions is obtained while the enlargement factors, the relative positions, and the rotation amounts are finely changed in respective predetermined ranges, and enlargement factors, relative positions, and rotation amounts which attain a maximum correlation value are obtained.

As described hereinabove, according to this embodiment, the combining processor 142 may generate a long-size image by appropriately combining a plurality of image data.

Third Embodiment

Next, a third embodiment will be described with reference to FIG. 9. The third embodiment is different from the first and second embodiments in that a defective region obtaining unit 144 which obtains a defective region in which adjacent two of radiation detection apparatuses overlap with each other from image data is provided.

The defective region obtaining unit 144 obtains defective regions representing structures (structure information) of radiation detection apparatuses 120 and 124 from image data (a radiation image) obtained by a radiation detection apparatus 122.

Specifically, the defective region obtaining unit 144 obtains image data of the radiation detection apparatus 122 which does not include information on an image of an object 100 from a storage unit 140. The defective region obtaining unit 144 determines regions in the image data obtained from the radiation detection apparatus 122 which include the structure information of the radiation detection apparatus 120 and the structure information of the radiation detection apparatus 124. Specifically, the defective region obtaining unit 144 recognizes region information of the structure information of the radiation detection apparatuses 120 and 124. Positional information of image data is included in the region information of the structure information of the radiation detection apparatuses 120 and 124. Then the defective region obtaining unit 144 outputs the defective region along with positional information to the image correction unit 146.

In a case where the radiation detection apparatuses 120 and 124 overlap with respective portions of the radiation detection apparatus 122, defective regions of the radiation detection apparatus 122 are obtained from image data obtained by the radiation detection apparatuses 120 and 124. Specifically, the defective region obtaining unit 144 determines image data of one of the radiation detection apparatuses 120, 122, and 124 from which a defective region is obtained in accordance with the layout relationship among the radiation detection apparatuses 120, 122, and 124. Here, the defective region obtaining unit 144 obtains a defective region of a certain radiation detection apparatus from image data obtained by a radiation detection apparatus arranged further from the radiation generation unit 112 when compared with the certain radiation detection apparatus. In other words, the defective region obtaining unit 144 does not obtain a defective region of image data obtained by a certain radiation detection apparatus from image data obtained by a radiation detection apparatus arranged closer to the radiation generation unit 112 when compared with the certain radiation detection apparatus.

The defective region obtaining unit 144 obtains a defective region from image data 302 obtained by the radiation detection apparatus 122. In a case where the radiation detection apparatuses 120, 122, and 124 are arranged and images thereof are captured in the state illustrated in FIG. 4, a portion of the radiation detection apparatus 122 overlaps with portions of the radiation detection apparatuses 120 and 124. Therefore, the image data obtained by the radiation detection apparatus 122 includes structure information of the radiation detection apparatuses 120 and 124. The defective region obtaining unit 144 obtains defective regions corresponding to the radiation detection apparatuses 120 and 124 from the image data obtained by the radiation detection apparatus 122.

As illustrated in FIG. 9, the image correction unit 146 performs a process of reducing the defective regions caused by the structure information of the radiation detection apparatuses 120 and 124 on a long-size image output from the combining processor 142. Specifically, the image correction unit 146 corrects the defective regions including the images of the portions of the radiation detection apparatuses 120 and 124 (the structure information of the radiation detection apparatuses 120 and 124).

Specifically, the image correction unit 146 recognizes the defective regions of the structure information of the radiation detection apparatuses 120 and 124 output from the defective region obtaining unit 144 and performs correction on the defective regions included in the composite image. The image correction unit 146 corrects the long-size image by reducing image defects in the defective regions using information on an image near the structure information of the radiation detection apparatuses 120 and 124. The information on the image near the structure information of the radiation detection apparatuses 120 and 124 is normal image information and is image information which does not include structure information. In this way, the image correction unit 146 may correct the long-size image by reducing the image defects included in the defective regions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

What is claimed is:

1. A radiographic system, comprising:
a plurality of radiation detection apparatuses configured to detect radial rays;
a combining processing unit configured to generate a long-size image by combining, with an adjustment of enlargement factors of a plurality of radiation images obtained by the plurality of radiation detection apparatuses; and
an image correction unit configured to correct a defective region including an image of a structure of each radiation detection apparatus of the plurality of radiation detection apparatuses in the long-size image,
wherein the combining processing unit and the image correction unit are implemented by at least one processor or circuitry.

2. The radiographic system according to claim 1, further comprising:
a radiographic stand on which the plurality of radiation detection apparatuses are disposed such that portions of the plurality of radiation detection apparatuses overlap with each other.

3. The radiographic system according to claim 1, further comprising:
a radiation generator that simultaneously emits radial rays to the plurality of radiation detection apparatuses.

4. The radiographic system according to claim 2, wherein:
the combining processing unit adjusts the enlargement factors of the plurality of radiation images based on a layout of the plurality of radiation detection apparatuses on the radiographic stand.

5. The radiographic system according to claim 1, further comprising:
a gradation processing unit implemented by at least one processor or circuitry and configured to perform a gradation process on the long-size image, which has been corrected by the image correction unit.

6. The radiographic system according to claim 1, further comprising:
a storage unit that stores the plurality of radiation images output from the plurality of radiation detection apparatuses, while determining, for each of the plurality of radiation images, whether image information of an object is included in the plurality of radiation images or not.

7. The radiographic system according to claim 6, wherein:
the storage unit stores the plurality of radiation images, which are simultaneously captured by the plurality of radiation detection apparatuses in an association with each other, and
the combining processing unit combines the plurality of radiation images with each other.

8. The radiographic system according to claim 1, further comprising:
a defective region obtaining unit implemented by at least one processor or circuitry and configured to obtain, from a radiation image obtained from one of the plurality of radiation detection apparatuses, a defective region representing structure information of the other of the plurality of radiation detection apparatuses.

9. The radiographic system according to claim 1, wherein:
the image correction unit corrects the defective region using information on a normal image region located adjacent to the defective region.

10. The radiographic system according to claim 1, wherein:
the image correction unit corrects a defective line included in the defective region using a normal line including a normal image region and adjacent to the defective line.

11. The radiographic system according to claim 10, wherein:
the image correction unit corrects the defective line by mixing a radiation image of the normal line with a radiation image of the defective line.

12. The radiographic system according to claim 10, wherein:
the image correction unit divides the defective region into defective lines in a unit of line, and repeatedly performs a correction process in the unit of line starting from an end line of the defective region, so that each of the defective lines approximates a pixel value distribution of a normal line, which is a portion of a normal region adjacent to the end line or a corrected defective line.

13. The radiographic system according to claim 10, wherein:
the image correction unit performs positioning between the defective region and the structure information indicating a structure of a radiation detection apparatus of the plurality of radiation detection apparatuses, and corrects the long-size image using defective information included in the structure information corresponding to the defective line included in the long-size image.

14. The radiographic system according to claim 1, wherein:
the image correction unit corrects the long-size image by generating two correction results by performing a correction in a bidirectional manner from lines adjacent to the defective region, with the defective region therebetween.

15. An image processing apparatus, comprising:
a combining processing unit configured to generate a long-size image by combining, with an adjustment of enlargement factors of a plurality of radiation images obtained by simultaneously emitting radial rays through an object to a plurality of radiation detection apparatuses having respective portions, which overlap with each other; and
an image correction unit configured to correct a defective region including an image of a structure of each radiation detection apparatus of the plurality of radiation detection apparatuses in the long-size image;
wherein the combining processing unit and the image correction unit are implemented by at least one processor or circuitry.

16. The image processing apparatus according to claim 15, wherein:
the combining processing unit adjusts the enlargement factors of the plurality of radiation images based on a layout of the plurality of radiation detection apparatuses.

17. The image processing apparatus according to claim 15, further comprising:
a gradation processing unit implemented by at least one processor or circuitry and configured to perform a gradation process on the long-size image, which has been corrected by the image correction unit.

18. An image processing method, comprising:
combining, with an adjustment of enlargement factors of a plurality of radiation images obtained by simultaneously emitting radial rays through an object to a plurality of radiation detection apparatuses having respective portions, which overlap with each other; and
correcting a defective region including an image of a structure of each radiation detection apparatus of the plurality of radiation detection apparatuses in the long-size image.

19. The image processing method according to claim 18, wherein:
the combining further comprises adjusting the enlargement factors of the plurality of radiation images based on a layout of the plurality of radiation detection apparatuses.

20. The image processing method according to claim 18, further comprising:
performing a gradation process on the long-size image, which has been corrected by the correcting.

* * * * *